United States Patent [19]

Yamauchi et al.

[11] 4,307,151
[45] Dec. 22, 1981

[54] ENZYME-ACTIVE FIBROUS MATERIALS AND METHOD FOR PREPARING SAME

[75] Inventors: Aizo Yamauchi, Atsugi; Tetsuro Suehiro, Yokohama; Mitsuo Suzuki; Mitsutaka Uzumaki, both of Tokyo; Masahiko Takashio, Fujieda, all of Japan

[73] Assignees: Director-General of the Agency of Industrial Science and Technology; Nitivy Co., Ltd., both of Tokyo, Japan

[21] Appl. No.: 65,330

[22] Filed: Aug. 9, 1979

[30] Foreign Application Priority Data

Aug. 30, 1978 [JP] Japan ............................... 53-105974
Aug. 30, 1978 [JP] Japan ............................... 53-105975

[51] Int. Cl.³ ........................ C12N 11/08; D02G 3/00
[52] U.S. Cl. .................................... 428/373; 428/374; 428/394; 435/180
[58] Field of Search ............... 428/364, 373, 374, 375, 428/394, 224, 400, 378; 435/180, 177, 288, 181; 8/115.5, 115.6

[56] References Cited

U.S. PATENT DOCUMENTS

| | | |
|---|---|---|
| 2,906,594 | 9/1959 | Osugi et al. ................... 526/319 X |
| 3,080,207 | 3/1963 | Tanabe et al. . |
| 3,084,989 | 4/1963 | Abe et al. . |
| 3,211,685 | 10/1965 | Fukushima et al. . |
| 3,741,724 | 6/1973 | Harmon . |
| 3,828,542 | 8/1974 | Boutonnet et al. ................ 428/374 |
| 3,904,478 | 9/1975 | Dean ............................ 435/181 X |

FOREIGN PATENT DOCUMENTS

50-145581  11/1975  Japan ................... 435/180

*Primary Examiner*—Lorraine T. Kendell
*Attorney, Agent, or Firm*—Brisebois & Kruger

[57] ABSTRACT

A novel enzyme-active fibrous material is proposed comprising fibers of a partially aminoacetalized polyvinyl alcohol as the support and an enzyme adsorbed and bonded thereto such as glucose isomerase, invertase, urease and the like. The enzyme-active fibrous material of the invention is readily prepared by dipping fibers of the partially aminoacetalized polyvinyl alcohol in an aqueous solution of the desired enzyme. The enzymatic activity and the physical properties of the fibers are remarkably improved by the use of extra-fine fibers prepared with composite fibers of a partially aminoacetalized polyvinyl alcohol and a polyethyleneoxide subjected to selective leaching away of the latter component or by the use of so-called sheath-and-core type or side-by-side type composite fibers of which one of the components is a partially aminoacetalized polyvinyl alcohol.

The enzyme-active fibrous materials of the invention can be used in various industrial processes utilizing enzymatic reactions very conveniently and with high efficiency.

7 Claims, 2 Drawing Figures

ENZYME-ACTIVE FIBROUS MATERIALS AND METHOD FOR PREPARING SAME

BACKGROUND OF THE INVENTION

The present invention relates to an enzyme-active fibrous material and a method for the preparation thereof or, in particular, the invention relates to a novel enzyme-active fibrous material comprising a partially aminoacetalized polyvinyl alcohol as a support and an enzyme bonded to the support and the method for the preparation thereof.

In several of the industrial manufacturing processes of various chemical substances by utilizing enzyme reactions, it is a recommendable way that the enzyme is used as a so-called "immobilized enzyme" composed of a suitable support material and the enzyme bonded to the support material in order to avoid the difficulties in handling of the water-soluble enzymes and separation of the enzyme and the reaction product after completion of the enzyme reaction as in the enzymatic preparation of various organic acids and saccharoses with advantages in the product qualities as well as in cost and energy saving. There are known several methods for the preparation of such "immobilized enzymes" including entrapping method, support method and crosslinking method, of which the support method is further classified into covalent bonding method, ionic bonding method and physical adsorption method. The immobilized enzymes prepared according to these methods are obtained usually in the form of a hydrated gel, films or granules, which are used as packed in a suitable reaction vessel such as a column and the reactant solution is passed through the bed of the immobilized enzyme in the column.

There have been proposed several immobilized enzymes prepared with certain fibrous supports such as a fibrous protein or hollow synthetic fibers of polyvinyl chloride, polyacrylonitrile, polysulfone and the like (see, for example, American Chemical Society, Symposium Series, volume 47, pages 100–131, 1977, and citations). The use of such a fibrous immobilized enzyme in enzyme reactions is advantageous in the easiness of packing and refilling of a reaction column therewith as well as in the easiness of the separation of the reactant solutions from the enzyme since the fibrous immobilized enzymes can be used in the form of a fabric such as woven cloths or non-woven fabrics. These fibrous immobilized enzymes in the prior art are, however, not satisfactory in the activity and durability of the activity as well as in the complicated procedure for the preparation thereof.

SUMMARY OF THE INVENTION

It is therefore an object of the present invention to provide a novel and improved fibrous immobilized enzyme or enzyme-active fibrous material with high activity and satisfactorily long serviceable life, which can be prepared in a simple procedure and the present invention has been established as a result of the extensive investigations undertaken by the inventors with the above object.

Thus, the present invention provides a novel enzyme-active fibrous material comprising a synthetic fiber of a partially aminoacetalized polyvinyl alcohol as a support material and an enzyme bonded thereto and a method for the preparation of the same by utilizing the remarkable affinity of the aminoacetalized polyvinyl alcohol (abbreviated as PVA hereinafter) fibers with various kinds of industrially useful enzymes.

The invention also proposes improved method for the preparation of enzyme-active fibrous materials with much improved activity and durability as well as mechanical strengths according to which extra-fine enzyme-active fibrous materials or fibers with composite structures are readily obtained.

BRIEF DESCRIPTION OF THE DRAWING

Curve I: fibers of partially aminoacetalized PVA with acid treatment

Curve II: fibers of partially aminoacetalized PVA without acid treatment

Curve III: hydrated gels of partially aminoacetalized PVA with acid treatment

Curve IV: hydrated gel of partially aminoacetalized PVA without acid treatment

Curve V: Duolite A-7 with acid treatment

Curve VI: Duolite A-7 without acid treatment

Curve I: fibers of partially aminoacetalized PVA

Curve II: Duolite A-7

DETAILED DESCRIPTION OF THE PREFERRED EMBODIMENTS

The support material as proposed by the inventors and suitable for the enzyme support is a synthetic fiber of a partially aminoacetalized PVA which is obtained by either spinning a PVA following partial aminoacetalization or spinning a PVA followed by partial aminoacetalization. The support fibers of the partially aminoacetalized PVA have preferably an equilibrium swelling ratio of 1.5 to 5.0 by weight in water at 30° C. The equilibrium swelling ratio is defined by the weight ratio of the fiber soaked in water at 30° C. for 24 hours or longer to attain a swelling equilibrium to the fiber in absolute dry.

The enzyme-active fibrous material of the invention is prepared, for example, by first aminoacetalizing a PVA to give a partially aminoacetalized PVA which is subjected to a process of wet spinning or dry spinning as an aqueous solution of 15 to 40% concentration to form fibers followed by subsequent drawing and/or heat treatment to have the equilibrium swelling ratio of 1.5 to 5.0 or, more preferably, 2.0 to 3.5 at 30° C. and dipping in an aqueous solution of the objective enzyme whereby the enzyme is firmly bonded to the fibers of the partially aminoacetalized PVA.

Alternatively, it is prepared by first spinning a PVA into fibers with following aminoacetalization which are subsequently subjected to drawing and/or heat treatment to have a desired equilibrium swelling ratio and dipped in the aqueous solution of the enzyme.

The PVA to be used in the above procedures has desirably an average degree of polymerization of 800 or larger and it may be a fully saponified PVA or a partially saponified PVA having a degree of saponification of 80% or larger by moles.

The aminoacetalization of PVA, either before or after the spinning, is performed in a homogeneous or heterogeneous phase by reacting with an aldehyde having an amino group or a substituted amino group or an acetal corresponding thereto. In this case, the reaction can be accelerated by the presence of a strong acid such as sulfuric acid or hydrochloric acid as a catalyst. It is also advantageous in some cases to perform the reaction in the presence of a swelling-reducing agent such as sodium sulfate or sodium chloride.

The above mentioned aldehyde having an amino group or a substituted amino group is exemplified by aminoacetaldehyde, monomethylaminoacetaldehyde, dimethylaminoacetaldehyde, trimethylmonoformylethylammonium halides, e.g. chloride, monoethylaminoacetaldehyde, diethylaminoacetaldehyde, triethylmonoformylethylammonium halides, e.g. chloride, 3-aminopropionaldehyde, 3-monomethylaminopropionaldehyde, aminobenzaldehydes, monomethylaminobenzaldehydes, dimethylaminobenzaldehydes and the like. The aminoacetalizing agents may be in the form of an acetal derived from the above listed aldehydes. Among the above named aminoacetalizing agents, dimethylaminoacetaldehyde or the acetals thereof and trimethylaminoacetaldehyde dimethylacetal bromide are preferred in most cases owing to the availability as well as moderate reactivity with PVA giving easy control of the reaction, although the selection of the aminoacetalizing agent depends on the particular enzyme to be bonded to the aminoacetalized PVA fibers. For example, trimethylaminoacetaldehyde dimethylacetal bromide is recommended when glucose isomerase is to be bonded.

The degree of the aminoacetalization is preferably at least about 0.5% by moles since an aminoacetalized PVA with smaller than about 0.5% by moles of the degree of aminoacetalization has poor affinity with the enzyme. On the other hand, the upper limit of the degree of aminoacetalization is given by the requirements on the spinnability of the aminoacetalized PVA and the equilibrium swelling ratio of the aminoacetalized PVA fibers. In this regard, the upper limit of the degree of aminoacetalization is about 10% by moles when the aminoacetalized PVA is to be subjected to spinning since an excessively aminoacetalized PVA has a decreased solubility in water so that spinning thereof cannot be performed without troubles and the upper limit is about 20% by moles when the aminoacetalization is to follow the spinning of an unaminoacetalized PVA in consideration of the equilibrium swelling ratio and the mechanical properties of the resultant fibers.

When the aminoacetalization precedes the spinning, the aminoacetalized PVA is dissolved in water in a concentration of 15 to 40% by weight and the aqueous solution is subjected to wet spinning or dry spinning in a conventional manner to give fibers of aminoacetalized PVA. It is optional, if desired, that the aqueous solution of the aminoacetalized PVA is admixed with an unaminoacetalized PVA with the object to adjust the content of the aminoacetal groups so as that the affinity of the support fibers with the enzyme is not excessively high.

When the aminoacetalization is performed with fibers of unaminoacetalized PVA, the fibers have desirably a softening point in water of 85° C. or higher and the reaction is carried out in an aqueous bath containing, for example, 15% by weight of sulfuric acid, 10% by weight of sodium sulfate and 10% by weight of the aminoacetalizing agent with a bath ratio of 1:50 at a temperature of 30° to 70° C. for 2 to 30 hours according to the desired degree of aminoacetalization. The degree of aminoactalization can be determined by the elementary analysis for nitrogen.

The synthetic fibers of the partially aminoacetalized PVA thus obtained are then subjected to drawing and/or heat treatment to be imparted with an equilibrium swelling ratio of 1.5 to 5.0 as given above. The equilibrium swelling ratio can be controlled by the selection of the drawing ratio or the temperature of the heat treatment. Usually, a drawing ratio of 400 to 500% and about 1 minute in hot air at 180° C. to 220° C. are sufficient to obtain a suitable equilibrium swelling ratio. When the equilibrium swelling ratio is smaller than 1.5, the fibers have poor affinity or adsorptivity to the enzyme so that the resultant enzyme-active fibrous material has insufficient activity. On the other hand, the fibers having an equilibrium swelling ratio larger than 5.0 have decreased mechanical strengths so that they are hardly used in an industrial process. It is of course optional that the fibers may be acetalized with formaldehyde or glutalic dialdehyde to increase the water-resistance and to control the equilibrium swelling ratio.

In the next place, the fibrous material of the partially aminoacetalized PVA with controlled equilibrium swelling ratio is dipped in an aqueous solution of a desired enzyme whereby the enzyme is adsorbed and bonded to the fibrous material as a support. The fibrous material is dipped in the enzyme solution as such or as chopped in a suitable fiber length as well as in a form of a woven or knit fabric, preferably, with agitation or shaking of the solution in order to ensure good contact of the enzyme solution and the fibrous material. In this treatment, the enzyme is fixed to the fibrous material by the formation of electric bonding due to the localization of the electrons or by the formation of ionic bonding with the amino or substituted amino groups in the fibrous material.

The enzymes suitable in the present invention are exemplified by glucose isomerases, invertases, ureases, glucoamilases, glucose oxidases, ribonucleases, proteases, lipases and the like although not specifically limited to the above named ones.

The conditions for the above immobilization reaction of enzymes on the fiber may differ widely from enzyme to enzyme. For example, the concentration of the enzyme in the enzyme solution is in the range from 0.01 to 1.0%, the temperature of the enzyme solution is from 5° to 60° C. and the time for dipping of the fibers is from 10 minutes to 24 hours.

It is recommendable in the preparation of the enzyme-active fibrous materials of the invention that the dipping treatment of the fibers of the partially aminoacetalized PVA is preceded by a treatment with an acid in order to increase the amount of the enzyme to be immobilized on the fibers. The acid may be an organic acid or an inorganic acid insofar as no deleterious effects are given on the mechanical properties of the fibers including, for example, hydrochloric acid, sulfuric acid, acetic acid, formic acid, phosphoric acid and the like in a concentration of about 0.2 to about 3.0 normal or, more preferably, 0.4 to 2.0 normal and in an amount of the acid equivalent to the aminoacetal groups in the fibrous material or larger. When the concentration of the acid solution is lower than about 0.2 normal, no sufficient improvement can be expected while higher concentrations than about 3.0 normal may result in markedly disadvantageous effects on the mechanical properties of the fibers. The acid treatment is performed usually at room temperature with sufficiently high velocities within, say, 10 to 20 hours since higher temperatures sometimes bring deleterious effects on the mechanical properties of the fibers treated with the acid.

By the above acid treatment, the adsorptivity of the fibrous material as the support for the enzyme is increased with a jump, say, up to an extent of 4 to 6 times in comparison with the untreated fibrous materials as the enzyme support with proportionally increased activity of the resultant enzyme-active fibrous material of the invention.

The enzyme active fibrous material of the invention obtained as described above having a fineness of 4 to 5 deniers per filament or a diameter of about 30 to 40 $\mu$m is advantageously used in various industrial enzymatic reactions with its high activity as well as with excellent durability of the activity along with sufficiently high mechanical strengths. Moreover the enzyme bonded to the partially aminoacetalized PVA can be readily desorbed or eluted out from the fibrous support material in a pH range at which no deactivation of the enzyme takes place in addition to the advantages of easy handling inherent to the fibrous materials.

It is a reasonable way that the activity of the enzyme-active fibrous material will be increased when the surface area of the fibrous support material is increased or the fiber diameter is decreased as far as possible to give a further improved industrial valuableness of the inventive enzyme-active fibrous materials. The inventors' investigations in this direction resulted in the establishment of a unique method according to which extra-fine fibers of a partially aminoacetalized PVA are readily obtained with a fiber diameter of 1 to 0.5 $\mu$m or even smaller to be used as a support material of the inventive enzyme-active fibrous materials. The above mentioned fiber diameter of 1 to 0.5 $\mu$m corresponds to a fineness of $8 \times 10^{-3}$ to $8 \times 10^{-5}$ denier/filament.

The extra-fine fibers of a partially aminoacetalized PVA is prepared by a process of dry spinning of an aqueous spinning solution containing a partially aminoacetalized PVA and a water-soluble amorphous polymeric substance into composite filaments which are then subjected to washing with water to leach away the water-soluble amorphous polymeric substance from the composite filaments leaving extra-fine fibers of the partially aminoacetalized PVA behind. Thus obtained extra-fine fibers have extraordinarily large specific surface area amounting to about 10 to 100 times of ordinary fibrous materials.

The water-soluble amorphous polymeric substances suitable for the above purpose are exemplified by polyethylene oxide, PVA of low degrees of saponification, e.g. 80 to 90% by moles, allyl-modified PVA with a degree of modification of 8 to 10% by moles, polypropylene oxide and the like.

The process for the preparation of the enzyme-active fibrous materials with the extra-fine fibers of the partially aminoacetalized PVA as the support is about the same excepting the presence of a water-soluble amorphous polymeric substance in the aqueous spinning solution and the leaching step with water of the composite filaments of the partially aminoacetalized PVA and the water-soluble amorphous polymeric substance. Alternatively, the extra-fine fibers of a partially aminoacetalized PVA may be obtained by first spinning an aqueous spinning solution containing an unaminoacetalized PVA and the water-soluble amorphous polymeric substance into composite filaments which are then subjected to leaching away of the water-soluble amorphous polymeric substance leaving extra-fine fibers of PVA followed by the aminoacetalization thereof.

The leaching of the water-soluble amorphous polymeric substance is performed, for example, by dipping the composite fibers in water with a bath ratio of 1:20 for 10 minutes followed by centrifugal separation of the water phase with repetition of the above procedure until no further weight decrease is observed in the remaining fibrous material.

The water-soluble amorphous polymeric substance suitable for the purpose is exemplified by polyethyleneoxides, PVAs of low degree, e.g., 80 to 90% by moles, of saponification, allylmodified PVAs, polypropylene oxides and the like, among which polyethyleneoxide is the most preferred. These water-soluble amorphous polymeric substances should have reasonable spinnability and good heat resistance to endure the thermal conditions in the spinning and subsequent heat treatment as well as not excessively high affinity with the PVA for the extra-fine fibers. The blending ratio of the water-soluble amorphous polymeric substance to the aminoacetalized or unaminoacetalized PVA is preferably in the range from 40:60 to 60:40 by weight in consideration of the balance of the desired fineness and the mechanical strengths of the resultant extra-fine fibers.

The fineness or the fiber diameter of the extra-fine fibers can be determined electronmicroscopically. The treatment of the extra-fine fibers of the partially aminoacetalized PVA with an aqueous solution of the desired enzyme can be performed in the same manner as described previously.

The enzyme-active fibrous materials prepared with the extra-fine fibers as the support material have sufficient mechanical strengths to be woven or knit into fabrics or to be processsed into paper-like sheets to be used in a similar manner to filter papers despite their extraordinary fineness. The remarkably enhanced specific surface area of the extra-fine fibers gives a markedly increased velocity for the adsorption or bonding of the enzyme on to the fibers and also exhibits very much increased activity in comparison with the same kind of the enzyme-active fibrous material but prepared with fibers of ordinary fineness in the practical use in industrial enzyme reactions.

Aside from the above described enzyme-active fibrous materials with greatly enhanced activity prepared with extra-fine fibers of the partially aminoacetalized PVA, an alternatively improved enzyme-active fibrous materials are proposed which are imparted with increased mechanical strengths as well as with very much reduced resistance against the flow of the reactant solutions owing to the structure or configuration of the fibers by means of utilizing a bicomponent or multicomponent fiber of which one component is the partially aminoacetalized PVA or a composite fiber including it. The polymeric substances forming the other component or components of the composite fiber are not limitative insofar as they have good mechanical properties and adequate compatibility with the partially aminoacetalized PVA to form a fiber with a composite structure and exemplified by unaminoacetalized PVA, copolymers of ethylene and vinyl acetate and the like.

The spinning techniques for forming the composite fibers are well known and the composite fibers may have any kinds of cross sectional configurations including the so-called side-by-side structure and the so-called sheath-and-core structure in which the partially aminoacetalized PVA constitutes the sheath portion and the other polymeric substance constitutes the core portion or vice versa.

To describe briefly the process for forming the composite fibers, a PVA is first partially aminoacetalized in a homogeneous or heterogeneous phase and separate aqueous spinning solutions are prepared with the partially aminoacetalized PVA and another polymeric substance for the other component of the composite fiber, which are simultaneously extruded from separate spinning nozzles known in the art for forming side-by-side composite fibers or sheath-and-core composite fibers either by wet spinning, dry spinning or semi-melt spinning.

The ratio of the amounts of the partially aminoacetalized PVA to the other polymeric substance is dependent on several factors but it is usually in the range from 20 to 60% by weight of the former to 80 to 40% by weight of the latter. It is because smaller proportions of the aminoacetalized PVA result in insufficient affinity of the resultant fibers as a whole to the enzyme as well as in the difficulty in preparing composite fibers from the technical standpoint of spinning while the composite fibers obtained with larger proportions of the aminoacetalized PVA have rather poor mechanical strengths unsuitable for certain industrial purposes. It is of course optional that the spinning solution containing the partially aminoacetalized PVA may be admixed with an unaminoacetalized PVA in order to control the content of the aminoacetal groups in the enzyme-affinitive portion of the composite fibers. The spinning nozzles used in the spinning of the composite fibers may have any suitable cross section known in the conventional spinning techniques for composite fibers of sheath-and-core type or side-by-side type.

The resultant composite fiber is then subjected to drawing and/or heat treatment to be imparted with sufficient mechanical strengths as well as with a suitable equilibrium swelling ratio in water. If desired, the thus obtained composite fiber is further acetalized with formaldehyde or glutalic dialdehyde to enhance the water-resistance and further treated with an aqueous acid solution of 0.2 to 3.0 normal or, preferably, 0.4 to 2.0 normal to enhance the activity for bonding the enzyme in the subsequent dipping of the fibers in an aqueous solution of the enzyme as is described previously.

The acid treatment described above is effective in increasing the adsorption of the enzyme on the composite fibers to an extent of 3 to 4 times or more with no decrease in the activity exhibition. The treatment is particularly effective for the sheath-and-core type composite fibers in which the core portion is a partially aminoacetalized PVA and the sheath layer is composed of an unaminoacetalized PVA giving even 5 times or more of the enzyme adsorption in comparison with the untreated fibers. An electronmicroscopic examination of the cross section of such an acid treated composite fiber indicated that the partially aminoacetalized PVA in the core had been partly leached away to form a macaroni-like hollow structure. It is presumable that the enzyme is effectively adsorbed on the inner surface of the thus obtained macaroni-like tubular fibers composed of the partially aminoacetalized PVA which is hydrophilic and highly affinitive with the enzymes and hardly crystallizable. On the other hand, the unaminoacetalized PVA in the sheath layer contributes to the mechanical strengths of the composite fibers after suitable drawing and heat treatment as in the ordinary PVA fibers.

Table 1 below gives the mechanical strengths and other properties of several of typical composite fibers prepared with a partially aminoacetalized PVA (denoted as A-PVA) containing 8% by moles of dimethylaminoacetal groups and an unaminoacetalized PVA (denoted simply as PVA) and subjected to 450% drawing and heat treatment at 210° C. The strength and the elongation were determined in water at 30° C.

TABLE 1

| Composite fiber | Strength g/denier | Elongation, % | Swelling ratio in water at 60° C. | % dissolved out in water at 60° C. |
|---|---|---|---|---|
| PVA (sheath)/A-PVA (core) by weight | | | | |
| 25/75 | — | — | 3.5 | 19.1 |
| 50/50 | 2.0 | 18.2 | 2.7 | 11.8 |
| 75/25 | 2.3 | 20.3 | 1.7 | 4.3 |
| A-PVA (sheath)/PVA (core) by weight | | | | |
| 25/75 | 2.0 | 19.3 | 1.8 | 4.5 |
| 50/50 | 1.9 | 30.1 | 2.7 | 12.9 |
| 75/25 | — | — | 3.5 | 17.1 |
| Side-by-side Type composite, A-PVA/PVA by weight | | | | |
| 25/75 | 2.4 | 17.3 | 1.7 | 5.5 |
| 50/50 | 2.0 | 19.5 | 2.5 | 10.5 |
| 75/25 | — | — | 3.3 | 16.8 |
| A-PVA single-component fiber | — | — | 10.1 | 33.1 |

Following are the examples to illustrate the present invention in further detail but not to limit the scope of the invention in any way. In the examples, the equilibrium swelling ratio in water, the softening point in water and the immobilized enzyme in % were determined as described below.

Equilibrium swelling ratio: the fiber sample was dipped in water at the indicated temperature for 24 hours followed by removal of excess water with a centrifugal separator rotating at 2000 r.p.m for 2 minutes and the swelling ratio was expressed as the ratio of the weight of the swollen fibers ($W_s$) to the weight of the fibers in absolute dry ($W_o$).

Softening point in water: the fiber was dipped in water and heated gradually at a rate of 1° C./minute until the fiber had contracted by 33% where the temperature was recorded.

Immobilized enzyme: the concentration of the enzyme in the aqueous solution after adsorption to the fibrous support material was determined to estimate the amount of the enzyme adsorbed on the support ($U_2$) and the immobilized enzyme was expressed in % by the ratio of $U_2$ to the amount of the enzyme in the aqueous solution $U_1$ before adsorption.

EXAMPLE 1

A PVA having an average degree of polymerization of 1,150 and a degree of saponification of 99.9% was acetalized with dimethylaminoacetaldehyde dimethylacetal to give about 8% by moles of the dimethylaminoacetal groups and dissolved in water by heating to give an aqueous solution of 30% concentration, which was then subjected to dry spinning into filaments.

The thus obtained filaments of the partially aminoacetalized PVA were drawn by 450% at 180° C. in air and then heat-treated at 210° C. to give a fibrous material for the enzyme support. The fibers had about 30 μm diameter and the equilibrium swelling ratio of them was about 4.23 by weight at 30° C.

The fibrous support material was washed thoroughly with deionized water and 1.5 g of the fibers as dry were dipped in 50 ml of an aqueous solution containing glucose isomerase exhibiting an activity of 736.2 GIU (glucose isomerase unit) and kept standing at 30° C. for 24 hours followed by washing with water at 30° C. until no enzyme was detected in the washing. It was found that the immobilized enzyme on the fiber support was 27.6%.

The enzymatic activity of the above obtained enzyme-active fibrous material was estimated by determining the isomerization of glucose in 50 ml of a 1-molar aqueous solution in which the fibrous material was dipped at 60° C. to give a result that the isomerization of the glucose into fructose was 33.6% after 22 hours.

EXAMPLE 2

The same fibrous material of the partially aminoacetalized PVA after drawing, heat treatment and washing with water as in Example 1 was dipped in a 2-normal aqueous solution of hydrochloric acid at room temperature for 5 hours followed by thorough washing with water. The procedures for the preparation of the enzyme-active fibrous material with the above obtained fiber support and the estimation of the activity for the isomerization of glucose into fructose were the same as in Example 1 to give that the immobilized enzyme was 38.8% and the isomerization of glucose into fructose was 49.3% showing that considerable improvement was obtained by the acid treatment.

EXAMPLE 3

A fibrous material obtained in the same manner as in Example 1 was chopped in 5 mm length and a glass column of 15 mm inner diameter and 34 cm length was packed with 10 g of the chopped fibers through which 200 ml of an aqueous solution of glucose isomerase exhibiting an activity of 180 GIU/ml was circulated at a space velocity of 3/hour at 40° C. for 18 hours to have the enzyme immobilized on the fiber support. The overall immobilized enzyme was 69%.

Through the thus obtained bed of the enzyme-active fibrous material as prepared was passed a 3-molar aqueous glucose solution continuously with a space velocity of 2/hour at 35° C. and the effluent solution was periodically analyzed for the determination of the isomerization of glucose into fructose to find that the value at the start was about 36 to 38% which was kept almost constant over a period of 14 days after starting.

EXAMPLE 4

The same aminoacetalized PVA as prepared in Example 1 was blended with equal amount of the same PVA before aminoacetalization and the polymer blend was processed into fibers with drawing and heat treatment in the same conditions as in Example 1. The thus obtained fibers had a fiber diameter of about 30 μm and an equilibrium swelling ratio of 1.9 at 30° C.

An enzyme-active fibrous material was prepared by shaking 0.2 g of the above obtained fibrous material with 20 ml of an aqueous solution of invertase with a pH of 6.0 as adjusted by use of a phosphate buffer solution and exhibiting an activity of 20 U/ml in a 50 ml Erlenmeyer flask at 30° C. for 20 hours followed by thorough washing with water to find that the immobilized enzyme was 60%.

The above obtained enzyme-active fibrous material was added into 50 ml of a 5% aqueous sucrose solution and the exhibited enzymatic activity of the fibrous material was estimated to correspond to 620 U/g as determined from the initial velocity of inversion, i.e. the activity of 0.2 g of the enzyme-active fibrous material was the same as 124 U of invertase dissolved in the solution.

EXAMPLE 5

An aqueous spinning solution containing 31% of a partially aminoacetalized PVA having a degree of acetalization of 3.5% by moles prepared by the acetalization of a PVA having an average degree of polymerization of 1,000 and a degree of saponification of 95.5% with trimethylaminoacetaldehyde dimethylacetal bromide and the spinning solution was extruded from a spinning nozzle into an atmosphere of hot air at 150° C. by the techniques of dry spinning into filaments.

The thus obtained filaments were subjected to drawing by 450% in air at 180° C. followed by heat treatment at 210° C. to give yellow-colored fibers with an equilibrium swelling ratio of 2.9 at 30° C. and a fineness of about 2 deniers.

A urease-active fibrous material was prepared by dipping 1.0 g of the above prepared fibrous support material in 30 ml of an aqueous urease solution with a pH of 8.0 as adjusted by use of a phosphate buffer solution and exhibiting an activity of 450 U/ml at 30° C. for 12 hours with shaking to find that 19% of the enzyme was immobilized on the fibrous support material.

The urease-active fibrous material was added in 50 ml of a 1% aqueous solution of urea and kept at 30° C. with formation of ammonia. The conversion of the urea into ammonia was about 20% after 1 hour.

EXAMPLE 6

A fully saponified PVA having an average degree of polymerization of 1,200 was acetalized with 4-aminobenzaldehyde to a degree of acetalization of 3% by moles and fibers were prepared by wet-spinning an aqueous spinning solution containing 15% of the above aminoacetalized PVA which was extruded from a spinning nozzle into a saturated aqueous solution of sodium sulfate at 50° C. followed by 400% drawing in hot air at 180° C. and heat treatment at 200° C. to give an equilibrium swelling ratio of 3.2 at 30° C.

An invertase-active fibrous material was prepared by shaking 5.0 g of the above prepared fibrous support material with 20 ml of an aqueous invertase solution with pH of 7.0 as adjusted by use of a phosphate buffer solution and exhibiting an enzymatic activity of 1,180 U/ml at 30° C. for 8 hours.

The activity of this invertase-active fibrous material was estimated by shaking 0.5 g of the fibrous material with 50 ml of a 5% aqueous sucrose solution at 30° C. for 5 hours to find that the inversion into glucose was 42%.

EXAMPLE 7

The invertase-active fibrous material prepared in Example 4 was packed in a column and an acetic acid solution buffered at pH 3.0 was continuously passed through the column. The invertase bonded to the fibers was gradually desorbed and eluted out to final desorption of about 80% of the enzyme without no marked loss in the enzyme activity indicating the ionic nature of the bonding between the enzyme and the fiber support as well as the reversibility in the adsorption and desorption of the enzyme giving an advantage in the recovery of the enzyme from a used material and reuse of the recovered enzyme.

EXAMPLE 8

A plain knit fabric with a basic weight of 110 g/m$^2$ was prepared with two-folded yarns of the fibers of about 30 μm diameter obtained in the same manner as in Example 1 followed by drawing and heat treatment. A piece of the above fabric weighing 10 g was soaked with 50 ml of an aqueous invertase solution of pH 6.0 exhibiting an activity of 236 U/ml and kept at 30° C. for 8 hours to give an invertase-active fibrous material. The immobilized enzyme was 85%.

Seven sheets of the above prepared invertase-active knit fabric was laid on the bottom of a glass column and a 5% aqueous sucrose solution was passed through the column at 30° C. with a space velocity of 4/hour as calculated in terms of the volume of the stacked sheets taking care to avoid peripheral leakage between the sheets and the column wall. The inversion of the sucrose in the effluent solution into glucose was about 44%.

EXAMPLE 9

Fibers of a partially aminoacetalized PVA were prepared in the same manner as in Example 1 except that the temperature of the heat treatment was 160° C. instead of 210° C. The equilibrium swelling ratio of the fibers in water was 4.5 at 30° C. The fibers was then formalized in a usual manner to have a degree of formalization of 30% by moles and an equilibrium swelling ratio of 1.9 at 30° C.

The same experimental procedures as in Example 1 indicated that the immobilized enzyme and the enzymatic activity of the enzyme-active fibrous material prepared with the fibers after formalization increased from 27.6% to 30.2% and from 33.6% to 35.6%, respectively, with remarkable improvement in the fiber strength from 1.2 g/denier to 2.3 g/denier as wet.

EXAMPLE 10

Partially aminoacetalized PVA fibers were prepared in the same maner as in Example 1 with drawing and heat treatment and 1.5 g of the fibers were dipped in 150 ml of 1-normal hydrochloric acid at 30° C. for 24 hours followed by thorough washing with deionized water. The thus acid-treated fibrous material was then dipped in 50 ml of an aqueous solution of glucose isomerase exhibiting an activity of 736.2 GIU at 30° C. for 24 hours followed by thorough washing with deionized water until no enzyme activity had been detected in the washing to give an enzyme-active fibrous material. The immobilized enzyme was 97.0%.

The test for the enzymatic activity of the fibrous material for the isomerization of glucose into fructose was undertaken in the same manner as in Example 1 to find that 51% of the glucose was isomerized after 22 hours with establishment of the isomerization equilibrium.

As is evident from the above results, the acid treatment is very effective in markedly increasing the immobilized enzyme as well as in improving the enzymatic activity of the enzyme-active fibrous material prepared with the acid-treated fibers in comparison with the untreated fibers.

EXAMPLE 11

The enzyme-active fibrous material with glucose isomerase prepared in the same manner as in Example 1 weighing 0.8 g as wet was packed in a stainless steel column of 4 mm inner diameter and 100 mm length and kept in a thermostat at 30° C. An aqueous glucose solution of 1-molar concentration was passed through the column at a rate of 30 ml/hour to find that the isomerization of the glucose in the effluent solution into fructose was 2.0%.

EXAMPLE 12

Each 1 g portions of the fibers of a partially aminoacetalized PVA prepared in the same manner as in Example 1 with drawing and heat treatment were dipped in $\phi$ml of a 1-normal solution of hydrochloric acid, sulfuric acid, acetic acid, phosphoric acid or formic acid at 30° C. for 6 hours followed by thorough washing with water and then shaken with 20 ml of an aqueous invertase solution exhibiting an activity of 100 U/ml at 30° C. for 8 hours with subsequent washing with water until no enzyme activity had been detected in the washing.

Each of the thus obtained enzyme-active fibrous materials was dipped in 50 ml of a 5% aqueous sucrose solution at 30° C. and the enzymatic activity was estimated from the inversion of the sucrose into glucose. The results are summarized in Table 2 below together with the results of the blank test in which the acid solution was replaced with pure water.

TABLE 2

| Acid | Immobilized enzyme | | Activity exhibition | |
|---|---|---|---|---|
| | U/g | % | U/g | % |
| Hydrochloric acid | 2000 | 100 | 944 | 47.2 |
| Sulfuric acid | 890 | 44.5 | 749 | 84.2 |
| Acetic acid | 1901 | 95 | 999 | 52.6 |
| Phosphoric acid | 2000 | 100 | 910 | 45.5 |
| Formic acid | 1745 | 87 | 971 | 55.6 |
| (Water) | 1001 | 50 | 339 | 33.9 |

EXAMPLE 13

A 1 g portion of the fibers prepared in Example 5 was dipped in 500 ml of 1-normal hydrochloric acid at 23° C. for 5 hours followed by thorough washing with water and then shaken with 20 ml of an aqueous solution of glucose isomerase buffered at pH 8.0 by use of a phosphate buffer solution and exhibiting an activity of 580 U/ml at 30° C. for 12 hours to give an enzyme-active fibrous material. The immobilized enzyme was 100%.

The enzymatic activity of the thus prepared fibrous material was 5,880 U/g for the isomerization of glucose corresponding to an activity exhibition of 50.7%.

For comparison, the same experimental procedure was repeated excepting the omission of the acid treatment resulting in an immobilized enzyme of 47% and an activity exhibition of 26%.

EXAMPLE 14

A 1 g portion of the fibers prepared in Example 5 was dipped in 100 ml of a 1.5-normal acetic acid solution at 25° C. for 5 hours followed by thorough washing with water and then shaken with 20 ml of an aqueous urease solution buffered at pH 8.0 by use of a phosphate buffer solution and exhibiting an activity of 450 U/ml at 30° C. for 12 hours to give a urease-active fibrous material. The immobilized enzyme was 100%.

The test for the enzymatic activity of the above prepared fibrous material was undertaken in the same manner as in Example 5 resulting in about 55% of conversion of the urea into ammonia at 30° C. after 1 hour to give an evidence for the effectiveness of the acid treatment in comparison with the results in Example 5.

EXAMPLE 15

Figure 1:
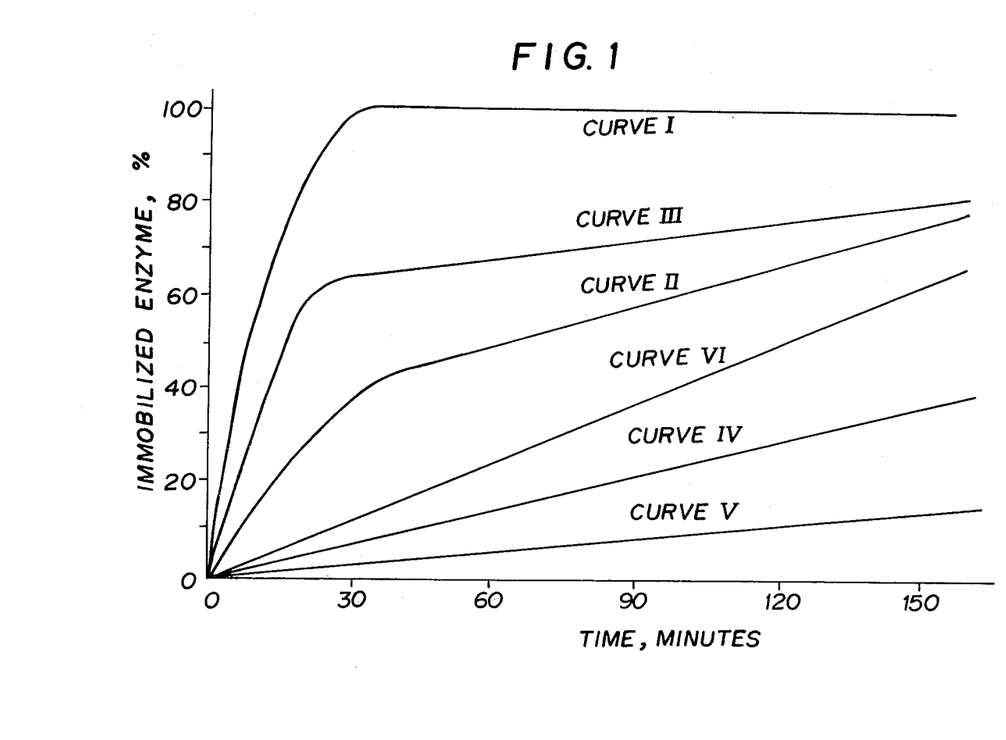
FIG. 1 is a graphic showing of the adsorption velocity of invertase on fibers of a partially dimethylaminoacetalized PVA, hydrated gel of the same partially dimethylaminoacetalized PVA and a weakly acidic ion exchange resin Duolite A-7 with or without acid treatment.

Each 1 g portions as dry of the fibers prepared in Example 1, a hydrated gel, which had been prepared by adding 5 ml of a 50% aqueous solution of glutalic dialdehyde into 100 ml of a 10% aqueous solution of the partially aminoacetalized PVA prepared in Example 1 followed by comminution with a homogenizer and washing, and a weakly basic anion exchange resin Duolite A-7 (product of Diamond Shamrock Chemical Co.) were dipped in 100 ml of 1-normal hydrochloric acid at 25° C. for 12 hours followed by thorough washing with water and then added to 50 ml of an aqueous invertase solution exhibiting an activity of 80 U/ml at 30° C. The same experimental procedure was undertaken with the same sample but without the acid treatment. Portions of the invertase solution were taken periodically to determined the residual activity of invertase from which the immobilized amount of invertase was calculated. The results are shown in FIG. 1. As is clear from the results, the acid treatment is effective not only for the fibrous material of the partially aminoacetalized PVA but also for the hydrated gel while not for the ion exchange resin. In particular, the velocity of adsorption of the enzyme was very rapid with the acid-treated fibrous material giving almost 100% of immobilized enzyme after 30 minutes.

EXAMPLE 16

A 1 g portion of the fibers prepared in Example 1 after drawing and heat treatment was dipped in 500 ml of 1-normal hydrochloric acid at 30° C. for 4 hours followed by thorough washing with water and then shaken with 20 ml of an aqueous invertase solution exhibiting an activity of 738 U/ml at 30° C. for 8 hours. The immobilized enzyme was 100%.

The invertase-active fibrous material above prepared was dipped in 50 ml of a buffered acetic acid solution with a pH of 2.8 at room temperature to find that the activity of the fibrous material decreased by 75% of the initial value after 5 hours while the solution gained an enzymatic activity approximately corresponding to the amount of invertase desorbed from the fibrous material indicating the reversibility of adsorption and desorption of the enzyme on the fibers of the partially aminoacetalized PVA.

EXAMPLE 17

A fully saponified PVA having an average degree of polymerization of 1,200 was subjected to dry spinning followed by 600% drawing at 190° C. to give filaments of a fineness of 120 deniers/50 filaments with a softening point in water of 92° C.

The filaments were dipped in an acetalizing solution containing 7% of hydrogen chloride, 15% of sodium chloride and 2% of dimethylaminoacetaldehyde dimethyl acetal in a bath ratio of 1:20 at 65° C. for 10 hours to give partially aminoacetalized PVA fibers containing 0.36% by weight of nitrogen corresponding to a degree of aminoacetalization of 2.3% by moles with an equilibrium swelling ratio in water of 2.5 at 30° C.

A 1 g portion of the thus obtained partially aminoacetalizated PVA fibers was dipped in 20 ml of an aqueous invertase solution exhibiting an activity of 100 U/ml at 30° C. for 5 hours to give an invertase-active fibrous material which was repeatedly washed with water. The enzymatic activity of the thus obtained invertase-active fibrous material was tested by dipping in 50 ml of a 5% aqueous sucrose solution buffered at pH 5.0 for 2 hours at room temperature to find that 48% of the sucrose was inverted into glucose.

EXAMPLE 18

Comparison of durability was undertaken with an inventive enzyme-active fibrous material and a weakly anionic ion exchange resin Duolite A-7. Thus, the enzyme-active fibrous material was prepared by the acetalization of a fully saponified PVA with dimethylaminoacetaldehyde dimethylacetal to a degree of acetalization of 8% by moles and spinning into fibers which were subjected to 450% drawing and a heat treatment at 230° C. to given an equilibrium swelling ratio of 2.06 at 30° C. followed by dipping in 1-normal hydrochloric acid for 8 hours.

Each 5 g portions of the fibers and the ion exchange resin were shaken with 25 ml aqueous solution of invertase exhibiting an activity of 236 U/ml at 30° C. for 18 hours to immobilize the enzyme on to the supports. The immobilization of the enzyme was complete for both of the support materials.

Figure 2:
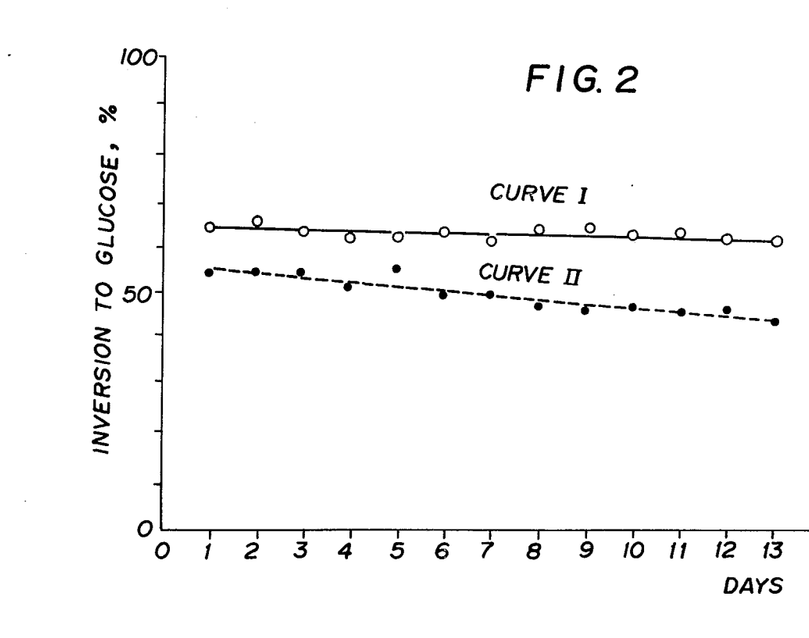
FIG. 2 shows the enzymatic activity of the invertase-active fibrous material in the inversion of sucrose to glucose and the durability of the activity in comparisin with a conventional ion exchange resin Duolite A-7.

A glass column of 10 mm inner diameter and 10 ml capacity was packed with 0.4 g of the enzyme-active fibrous material or 2.7 g of the enzyme-active ion exchange resin and a 5% aqueous solution of sucrose was passed through the column at 30° C. continuously with a space velocity of 1 to 2 per hour. The effluent solution was analyzed periodically to determine the inversion of sucrose to glucose over a period of 13 days. The results are shown in FIG. 2, from which it is evident that the activity of the inventive fibrous material was very stable over the period while the activity of the ion exchange resin decreased gradually.

EXAMPLE 19

Preparation of extra-fine fibers of a partially aminoacetalized PVA

A polymer blend having an average content of the aminoacetal groups equal to 1.0% by moles was prepared by blending 15.4 parts by weight of a partially aminoacetalized PVA with a degree of aminoacetalization of 6.5% by moles prepared in a heterogeneous phase with dimethylaminoacetaldehyde and 84.6 parts by weight of a fully saponified PVA having an average degree of polymerization of 1,200 and a first aqueous spinning solution was prepared by dissolving the above PVA blend in hot water in a concentration of 34% by weight. On the other hand, a second aqueous spinning solution was prepared by dissolving a polyethyleneoxide (hereinafter abbreviated as PEO) having an average molecular weight of 400,000 in water in a concentration of 32% by weight.

A composite filament was prepared by the technique of dry spinning with the weight ratio of the PVA blend/PEO equal to 45:55 by intermixing both of the spinning solutions directly before the exit of the spinning nozzle with a static mixer with subsequent 450% drawing and heat treatment at 230° C. to give composite filaments with a fineness of 150 deniers/30 filaments composed of the PVA blend and PEO.

The composite filament was then washed with water to leach away the PEO and to leave extra-fine fibers of the PVA blend with diameters ranging from 0.05 to 1 μm as examined by electronmicroscopy, which were subjected to formalization in a formalizing bath composed of 20% by weight of sulfuric acid, 20% by weight of sodium sulfate, 2% by weight of formaldehyde and 58% by weight of water at 40° C. for 1 hour.

For comparative purpose, fibers of the above PVA blend with ordinary fineness of about 30 μm diameter were prepared with the above first spinning solution without intermixing with the second PEO spinning solution, the other conditions being the same as in the above for the preparation of the extra-fine fibers.

The thus obtained two kinds of the support fibers were tested for the softening point in water, equilibrium swelling ratio, adsorption velocity of enzyme and adsorption velocity of dyestuff to give the results set out in Table 3 below. In the table, the adsorption velocity of enzyme was determined by dipping 1 g portions each of the support fibers in 50 ml of an aqueous invertase solution buffered at a pH of 6.0 by use of a phosphate buffer solution and exhibiting an activity of 1,260 U/ml at 30° C. and recording the time taken for the 50% adsorption of the invertase and the adsorption velocity of dyestuff was determined by dipping 10 g portions each of the support fibers in 500 ml of an aqueous solution containing 0.5% owf (on the weight of fibers) of Suminol Fast Sky Blue B (tradename, product of Sumitomo Chemical Co., Japan) at 60° C. and recording the half-dyeing time.

TABLE 3

| Fineness of fibers | Softening point in water, °C. | Equilibrium swelling ratio in water at 30° C. | Equilibrium swelling ratio in water at 80° C. | Adsorption velocity of enzyme, minutes | Adsorption velocity of dyestuff, minutes |
| --- | --- | --- | --- | --- | --- |
| Extra-fine | 110 | 2.7 | 2.8 | 20 | 0.5 |
| Ordinary | 108 | 1.9 | 2.5 | 180 | 25 |

EXAMPLE 20

A spinning solution in a concentration of 38% by weight was prepared by dissolving in water 55 parts by weight of a PEO having an average molecular weight of 250,000 and 45 parts by weight of a PVA blend composed of equal amounts of a partially aminoacetalized PVA obtained by heterogeneous aminoacetalization with dimethylaminoacetaldehyde and having a degree of aminoacetalization of 5.5% by moles and a fully saponified PVA having an average degree of polymerization of 1,200.

Composite filaments of the PVA blend/PEO were prepared by dry-spinning the above spinning solution followed by 450% drawing and heat treatment at 230° C. to give a fineness of 140 deniers/30 filaments, which were then wased with water to leach away the PEO and to leave extra-fine fibers of the PVA blend having a fineness of $3.5 \times 10^{-4}$ denier/filament or about 0.2 μm in diameter.

On the other hand, fibers of the PVA blend with a fineness of 120 deniers/40 filaments were prepared by dry-spinning a spinning solution containing 35% by weight of the same PVA blend as above, the other conditions being the same as in the above for the preparation of the extra-fine fibers. The specific surface area as calculated, softening point in water and equilibrium swelling ratio in water at 30° C. are shown in Table 4 below.

Enzyme-active fibrous materials were prepared by shaking 1 g portions each of the above support fibers with 50 ml of an aqueous invertase solution exhibiting an activity of 2,600 U/50 ml at 30° C. for 24 hours followed by washing with water until no enzymatic activity has been detected in the washing and subjected to the test for the enzymatic activity by determining the inversion velocity of sucrose into glucose when the invertase-active fibrous material above prepared was dipped in 50 ml of a 5% by weight aqueous solution of sucrose at 30° C. The results are set out also in Table 4.

TABLE 4

| Fineness of fibers, denier/filament | Specific surface area (calculated), m²/g | Softening point in water, °C. | Equilibrium swelling ratio in water at 30° C. | Invertase-active fibers Immobilized enzyme, % | Invertase-active fibers Activity exhibition, U/g |
| --- | --- | --- | --- | --- | --- |
| $3.5 \times 10^{-4}$ | 15.7 | 60 | 3.1 | 100 | 791 |
| 3 | 0.17 | 62 | 2.5 | 65 | 546 |

EXAMPLE 21

An aqueous spinning solution of an overall solid content of 36% by weight was prepared by dissolving in water with heating 45 parts by weight of a partially aminoacetalized PVA having an average degree of polymerization of 1,200 and a degree of aminoacetalization of 2.2% by moles and 55 parts by weight of a PEO having an average molecular weight of 300,000. This spinning solution was subjected to dry spinning into filaments, which were drawn by 450% and heat-treated at 230° C. to give composite fibers of aminoacetalized PVA/PEO with a fineness of 150 deniers/40 filaments corresponding to a fiber diameter of 21 μm in an average.

The thus obtained fibers were washed with water whereby the PEO component was leached away to leave extra-fine fibers of the aminoacetalized PVA with an average diameter of 0.15 μm, a softening point of 62° C. in water and an equilibrium swelling ratio of 2.5 in water at 30° C.

On the other hand, fibers of ordinary fineness were prepared with the same partially aminoacetalized PVA as used above with drawing and heat treatment. These comparative fibers had a fineness of 120 deniers/40 filaments, average fiber diameter of 18.5 μm, softening point of 60° C. in water and equilibrium swelling ratio of 2.3 in water at 30° C.

Urease-active fibrous materials were prepared by dipping 1 g portions each of the above obtained fibrous materials in 20 ml of an aqueous solution of urease exhibiting an activity of 450 U/ml at 30° C. for 24 hours followed by thorough washing with water.

The above prepared urease-active fibrous material was added in 50 ml of an aqueous urea solution of 1% concentration at 30° C. and the amount of ammonia produced after 1 hour was determined from which the conversion of urea into ammonia was calculated. The results are set out in Table 5 below.

TABLE 5

| Fineness of fibers | Immobilized enzyme U/g | % | Urea conversion after 1 hour, % |
|---|---|---|---|
| Extra-fine | 9,000 | 100 | 52 |
| Ordinary | 3,870 | 43 | 23 |

EXAMPLE 22

The extra-fine fibers and fibers of ordinary fineness prepared as the enzyme supports in the preceding example were formalized by dipping in an formalizing bath composed of 20% by weight of sulfuric acid, 20% by weight of sodium sulfate, 2% by weight of formaldehyde and 58% by weight of water at 30° C. for 3 hours to be imparted with enhanced resistance against hot water.

Enzyme-active fibrous materials were prepared with the thus formalized support fibers by dipping 1 g portions each of them in 50 ml of an aqueous solution of glucose isomerase having a pH value as adjusted to 8.3 and exhibiting an activity of 780 CIU/50 at 30° C. for 24 hours followed by thorough washing with water.

The thus prepared enzyme-active fibrous materials were added each in 50 ml of a 1-molar aqueous solution of glucose at 60° C. and kept for 24 hours to determined the isomerization of glucose into fructose. The results are set out in Table 6 below together with the properties of the fibrous materials.

TABLE 6

| Fineness of fibers | Softening point in water, °C | Equilibrium swelling ratio in water at 60° C. | Enzyme-active fibers Immobilized enzyme U/g | Enzyme-active fibers Activity exhibition, % | Glucose isomerization to fructose, U/g | % |
|---|---|---|---|---|---|---|
| Extra-fine | 96 | 2.8 | 755 | 97 | 604 | 50 |
| Ordinary | 95 | 2.4 | 179 | 23 | 63.5 | 35.5 |

EXAMPLE 23

A 34% by weight aqueous solution of a fully saponified PVA with an average degree of polymerization of 1,200 and a 30% by weight aqueous solution of PEO with an average molecular weight of 750,000 were subjected to dry spinning simultaneously by blending just before the spinning nozzle with a static mixer of 20 elements in such a proportion that the weight ratio of PVA/PEO as solid is equal to 48/52 with subsequent 450% drawing and heat treatment at 235° C. to give PVA/PEO composite filaments of 160 deniers/40 filaments fineness.

A plain knit fabric was prepared with the above obtained filaments and washed with water whereby the PEO was leached away to leave extra-fine fibers of PVA with a fineness ranging from 0.05 to 1 μm in diameter. The thus treated fabric of extra-fine PVA fibers was dipped in an acetalizing bath composed of 5% by weight of hydrogen chloride, 15% by weight of sodium chloride, 0.3% by weight of dimethylaminoacetaldehyde and 79.7% by weight of water in a bath ratio of 1:20 at 60° C. for 8 hours to give a partially aminoacetalized PVA with a degree of aminoacetalization of 2.8% by moles. These extra-fine fibers of the partially aminoacetalized PVA had a softening point of 65° C. in water and an equilibrium swelling ratio of 3.2 in water at 30° C.

A piece of the thus obtained knit fabric weighing 1 g was dipped in 50 ml of an aqueous solution of invertase with a pH of 6.0 and exhibiting an activity of 4000 U/50 ml at 30° C. for 24 hours followed by thorough washing with water to give an invertase-active knit fabric. The immobilized enzyme was 100%.

This invertase-active knit fabric was added to 50 ml of a 5% by weight aqueous solution of sucrose at 30° C. and the enzymatic activity estimated from the initial velocity of inversion of sucrose to glucose was 1,580 U/g or 25.3%.

EXAMPLE 24

An invertase-active extra-fine fibrous material was prepared with the fibrous support material used in Example 20 by dipping 1 g portion of the support in 20 ml of an aqueous solution of invertase exhibiting an activity of 200 U/ml at 30° C. for 24 hours. The immobilized enzyme was 100%.

The invertase-active fibrous material was packed in a glass column of 16 mm inner diameter and 100 mm length and a 5% aqueous sucrose solution with a pH of 6.0 was passed at 30° C. continuously with a space velocity of 2.2/hour. The inversion of sucrose in the effluent solution was determined to find that the enzymatic activity was so high that the inversion at the beginning was almost 100% and the activity lasted over a period of 60 days of continued running without no remarkable decrease in the activity.

EXAMPLE 25

Composite filaments composed of equal amounts of a partially aminoacetalized PVA obtained by aminoacetalizing a PVA having a degree of saponification of 99.9% and an average degree of polymerization of 1,150 with dimethylaminoacetaldehyde dimethyl acetal to give a degree of acetalization of 8% by moles and the same PVA before aminoacetalization were prepared by spinning equal amounts of two spinning solutions containing each 30% by weight of one of the above mentioned polymers simultaneously by use of a spinning nozzle for sheath-and-core type composite filaments.

Two types of the composite filaments were prepared as described above, in which the sheath layer is composed of the partially aminoacetalized PVA and the core is composed of the unacetalized PVA or vice versa. The weight ratio of the two polymers was 50:50 in each of the above two types. These filaments were subjected to drawing by 450% in air at 180° C. and, finally, to a heat treatment at 210° C. The physical properties of these drawn and heat-treated filaments are set out in Table 7 below together with the properties of a single-component filaments of the same partially aminoacetalized PVA.

After thorough washing with water, 1 g portions each as dry of these three kinds of fibers were dipped in 25 ml of an aqueous solution of glucose isomerase exhibiting an activity of 383 GIU/ml at 30° C. for 12 hours to give enzyme-active fibrous materials followed by repeated washing with water until no enzymatic activity had been detected in the washing.

The enzymatic activity of these fibrous materials was determined by measuring isomerization of glucose into fructose when the fibrous material was dipped in 50 ml of an aqueous 1-molar solution of glucose at 60° C. for 22 hours. The results are also set out in Table 7.

TABLE 7

| Fibers | Fiber strength, g/denier | | Elongation, % | | Immobilized enzyme, % | Glucose isomerization, % |
|---|---|---|---|---|---|---|
| | dry | wet | dry | wet | | |
| (A) | 4.3 | 1.9 | 25 | 28 | 82.2 | 28.6 |
| (B) | 4.5 | 2.0 | 25 | 22 | 46.8 | 26.4 |
| (C) | 3.2 | 0.5 | 27 | — | 93.0 | 31.5 |

(A) Partially aminoacetalized PVA (sheath)/PVA(core) composite fibers
(B) PVA (sheath)/partially aminoacetalized PVA (core) composite fibers
(C) Single-component fibers of partially aminoacetalized PVA

EXAMPLE 26

Portions of the composite fibers (A) and (B) prepared in the preceding example each weighing 1 g as dry were dipped in 100 ml of 1-normal hydrochloric acid at 30° C. for 24 hours followed by washing with water to neutral and then dipped in 50 ml of an aqueous solution of glucose isomerase exhibiting an activity of 740 GIU/ml at 30° C. for 24 hours and washed with water repeatedly until no enzymatic activity had been detected in the washing to give enzyme-active fibrous materials. The enzymatic activity of these fibrous materials was tested in the same manner as in Example 25 to give the results as set out in Table 8 below.

Incidentally, the single-component fibers of the same partially aminoacetalized PVA could not retain their fibrous form after treatment with the diluted hydrochloric acid exhibiting swelling and contraction to a large extent.

TABLE 8

| Fibers | Immobilized enzyme, % | Glucose isomerization, % |
|---|---|---|
| (A) | 97 | 51 |
| (B) | 98 | 51 |

As is understood from the results given in Table 8 in comparison with the results in the preceding example, the acid treatment was so effective that complete isomerization equilibrium had been established after 22 hours of the reaction with larger amounts of the immobilized enzyme than without acid treatment. This effect of acid treatment was particularly remarkable with the composite fibers (B) having the sheath layer of unaminoacetalized PVA and the core of the partially aminoacetalized PVA. An electronmicroscopic examination of cross sections of the composite fibers (B) after the acid treatment indicated that the partially aminoacetalized PVA in the core had been partly dissolved out leaving a tubular fiber structure something like a macaroni in which the partially aminoacetalized PVA was exposed bare on the inner surface of the tubular structure.

EXAMPLE 27

Composite fibers with the same partially aminoacetalized PVA as the sheath layer and the same unacetalized PVA as the core as in the composite fibers (A) in Example 25 were prepared in the same manner except that the weight ratio of the sheath layer and the core was varied in the range of 20 to 60% of the former to 80 to 40% of the latter followed by the same drawing and heat treatment as in Example 25.

Enzyme-active fibrous materials were prepared by dipping 1.5 g portions each of the above obtained composite fibers in 50 ml of an aqueous solution of glucose isomerase exhibiting an activity of 615 GIU at 30° C. for 18 hours followed by repeated washing with water at 30° C. until no enzymatic activity had been detected in the washing.

The enzymatic activity of these fibrous materials was tested in the same manner as in Example 25 by dipping 1 g portions each of the fibrous materials in 50 ml of a 1-molar aqueous glucose solution at 60° C. for 20 hours. The results are summarized in Table 9 below.

TABLE 9

| Fiber, sheath/core weight ratio | Fiber strength, g/denier | | Equilibrium swelling ratio in water at 60° C. | Immobilized enzyme, % | Glucose isomerization, % |
|---|---|---|---|---|---|
| | dry | in water at 60° C. | | | |
| 20/80 | 4.5 | 3.0 | 1.56 | 25.8 | 9.2 |
| 40/60 | 4.3 | 2.5 | 1.97 | 65.7 | 15.3 |
| 60/40 | 3.8 | 1.5 | 5.29 | 90.0 | 28.5 |
| 80/20 | 3.7 | 0.3 | 9.03 | 91.5 | 29.5 |
| Single-component fibers (*) | 3.2 | — | — | 93.0 | 31.5 (**) |

(*) Single-component fibers of the same partially aminoacetalized PVA
(**) After 22 hours As is understood from the results given in Table 9, smaller composite ratios than 20% of the partially aminoacetalized PVA results in marked decrease in the affinity of the fibers with the enzyme while composite fibers with the ratio larger than 60% have poor mechanical properties or, especially, fiber strength in hot water so as to affect the practicability of the fibers adversely.

EXAMPLE 28

The same procedure for the preparation of composite fibers was repeated as in Example 25 except that one of the spinning solutions contained a 50:50 by weight blend of the same partially aminoacetalized PVA and the same unacetalized PVA instead of the partially aminoacetalized PVA alone. The thus obtained composite fibers had substantially the same physical properties as those prepared in Example 25.

Each 0.5 g portions of the thus prepared fibrous materials was shaken with 50 ml of an aqueous solution of invertase with a pH as adjusted to 6.0 by use of a phosphate buffer solution and exhibiting an activity of 1,180 U/g in a 50 ml Erlenmeyer flask at 30° C. for 22 hours to give invertase-active fibrous materials followed by thorough washing with water.

The enzymatic activity of these fibrous materials was estimated by determining the initial velocity of the sucrose inversion to glucose when each of the fibrous materials was added in 50 ml of a 5% aqueous sucrose solution at 30° C. to give the results as set out in Table 10 below.

The same experimental procedures as above were repeated except that each of the fibrous materials was dipped in 100 ml of 1-normal hydrochloric acid at 40° C. for 16 hours before it was subjected to treatment with the invertase solution. The results are also given in Table 10.

As is clear from these results, the acid treatment is effective in increasing the immobilized enzyme as well as the activity exhibition. The effects are more remarkable for the composite fibers with the core of the partially aminoacetalized PVA than for the other type of the composite fibers.

TABLE 10

| Composite fibers | Without acid treatment | | With acid treatment | |
|---|---|---|---|---|
| | Immobilized enzyme, % | Activity exhibition, U/g | Immobilized enzyme, % | Activity exhibition, U/g |
| (A) | 83 | 325 | 100 | 450 |
| (B) | 69 | 283 | 100 | 580 |

(A) partially aminoacetalized PVA (sheath)/unaminoacetalized PVA (core)
(B) unaminoacetalized PVA (sheath)/partially aminoacetalized PVA (core)

The enzyme-active fibrous materials prepared above were washed in a column continuously with an acetic acid buffer solution of pH 3.0 to find that the enzyme immobilized thereon was gradually eluted out up to 80% of the initially immobilized amount indicating the predominantly ionic nature of the bonding between the enzyme and the support. The thus eluted enzyme exhibited almost the same activity as before.

EXAMPLE 29

Composite fibers of side-by-side type with a fineness of 100 deniere/25 filaments were prepared with the same partially aminoacetalized PVA and the same PVA as used in Example 25 in equal amounts followed by drawing and heat treatment in the same manner. The physical properties of these composite fibers were substantially the same as in Example 25.

Further, these composite fibers were subjected to the acid treatment in the same manner as described in Example 26.

Preparation of enzyme-active fibrous materials with these composite fibers and testing of the enzymatic activity thereof were undertaken in the same manner as in Example 28 to give the results set out in Table 11 below. As is clear from the results, the side-by-side type composite fibers have the same degree of affinity with the enzyme as the sheath-and-core type composite fibers.

TABLE 11

| Acid treatment | No | Yes |
|---|---|---|
| Immobilized enzyme, % | 63 | 100 |
| Activity exhibition, U/g | 295 | 425 |

EXAMPLE 30

The composite fibers (A) prepared in Example 25 were chopped in 5 mm length and a 10 g portion of the chopped fibers was packed in a glass column of 15 mm inner diameter and 300 mm length. Then 250 ml of an aqueous solution of glucose isomerase with a pH of 8.0 as adjusted with a phosphate buffer solution and exhibiting an activity of 165 GIU/ml was passed and circulated through the bed of the chopped fibers at 40° C. with a space velocity of 4.5/hour for 20 hours to have the enzyme immobilized on the fibrous material. The immobilized enzyme was 72% of the amount initially contained in the enzyme solution.

The enzymatic activity of the enzyme-active fibrous material was tested by passing a 3-molar aqueous solution of glucose continuously at 60° C. with a space velocity of 1.5/hour through the bed of the enzyme-active chopped fibers. The isomerization of the glucose in the effluent solution was 41 to 45% at the beginning of the run and remained almost constant even after 2 weeks of the continued run. The crimps of the fibrous material were retained after chopping so that the resistance of the bed of the chopped fibers against liquid flow was very small without substantial back pressure permitting free control of the space velocity along with easiness in packing into and taking out of the column.

EXAMPLE 31

Aqueous spinning solutions of each 33% concentration were prepared with a partially aminoacetalized PVA obtained by aminoacetalizing a PVA with an average degree of polymerization of 1,000 and a degree of saponification of 95.5% with trimethylaminoacetaldehyde dimethylacetal bromide to a degree of acetalization of 4% by moles and with an unacetalized PVA with an average degree of polymerization of 1,100 and a degree of saponification of 99.9%. These spinning solutions were subjected to dry spinning by extruding simultaneously from a nozzle for sheath-and-core type composite fibers into hot air at 150° C. in a composite ratio of 50:50 by weight, the sheath layer being composed of the partially aminoacetalized PVA and the core being composed of the unacetalized PVA, followed by 450% drawing in air at 190° C. and heat treatment at 210° C. The resultant fibers had a fineness of 2.5 deniers/filament.

A portion of the thus obtained composite fibers weighing 1 g was shaken with 50 ml of an aqueous solution of urease with a pH of 8.0 as adjusted with a phosphate buffer solution and exhibiting an activity of 320 U/ml at 30° C. for 20 hours to give a urease-active fibrous material. The immobilized enzyme was 35%.

This urease-active fibrous material was added to 50 ml of a 1% aqueous solution of urea and kept at 30° C. to detect the formation of ammonia. The conversion of urea to ammonia was 28% after 1 hour.

EXAMPLE 32

Aqueous spinning solutions of each 15% by weight concentration were prepared with the same partially aminoacetalized PVA and the same PVA as used in Example 25 and subjected to wet spinning by extruding from a spinning nozzle for sheath-and-core type composite fibers, the sheath layer being composed of the partially aminoacetalized PVA, into an aqueous saturated solution of sodium sulfate, the weight proportion of both spinning solutions being 50:50, followed by 450% drawing in hot air at 180° C. and heat treatment at 200° C.

An enzyme-active fibrous material was prepared by shaking 1 g portion of the above obtained support fibers, after acid treatment by dipping in 100 ml of 1-normal hydrochloric acid at 40° C. for 8 hours with subsequent thorough washing with water, with 25 ml of an aqueous solution of invertase exhibiting an activity of 118 U/ml at 30° C. for 20 hours. The immobilized enzyme was 100%.

The thus prepared enzyme-active fibrous material was dipped in 50 ml of a 5% by weight aqueous sucrose solution at 30° C. and the enzymatic activity estimated from the initial velocity of inversion of sucrose to glucose was 920 U/g.

EXAMPLE 33

A plain knit fabric with a basis weight of 105 g/m² was prepared with two-folded yarns of the composite fibers (A) obtained in Example 25. A piece of this knit fabric weighing 10 g was dipped in 500 ml of 1-normal hydrochloric acid at room temperature for 18 hours followed by thorough washing with deionized water and shaken with 75 ml of an aqueous solution of invertase exhibiting an activity of 55 U/ml at 30° C. for 18 hours to give an invertaseactive fibrous material. The immobilized enzyme was 96%.

The thus obtained enzyme-active knit fabric was cut into 10 circular sheets of each 3 cm diameter and they were laid on the bottom of a column of 3 cm inner diameter and 5% by weight aqueous solution of sucrose was passed through the layers of the fabric sheets at 30° C. with a space velocity of 2/hour taking care to avoid any peripheral leakage. The inversion of sucrose into glucose in the effluent solution was 46%. The resistance of the fabric layers against the liquid flow was negligible and the space velocity can be increased up to 5/hour or higher without substantial back pressure and without substantial decrease in the inversion of sucrose into glucose.

EXAMPLE 34

The sheath-and-core type composite fibers (B) prepared in Example 25 were subjected to formalization in a usual manner to a degree of formalization of 25% by moles whereby the equilibrium swelling ratio in water at 30° C. decreased from 3.38 to 2.02. The fibers had a strength of 3.6 g/denier as dry or 2.8 g/denier as wet.

The immobilization of glucose isomerase and the test for the activity of the thus prepared enzyme-active fibrous material were carried out in the same manner as in Example 25 to give the results that the immobilized enzyme was 45.3% and the isomerization of glucose was 28.6%.

EXAMPLE 35

Each 1 g portions of the composite fibers (A) prepared in Example 25 were dipped in 100 ml of a 1-normal aqueous solution of hydrochloric acid, sulfuric acid, acetic acid, phosphoric acid or formic acid at 30° C. for 10 hours followed by thorough washing with deionized water and then shaken with 25 ml of an aqueous invertase solution exhibiting an activity of 80 U/ml at 30° C. for 18 hours with subsequent washing with water repeatedly until no enzymatic activity had been detected in the washing to give invertase-active fibrous materials.

Each of the thus prepared invertase-active fibrous materials was dipped in 50 ml of a 5% by weight aqueous solution of sucrose at 30° C. and the enzymatic activity was estimated from the initial velocity of sucrose inversion into glucose. The results for various acid treatments as well as for the blank test with pure water instead of an acid solution are set out in Table 12 below. As is clear from the results, the acid treatment is effective in increasing the immobilized enzyme and the activity exhibition.

TABLE 12

| Acid | Immobilized enzyme | | Activity exhibition | |
| --- | --- | --- | --- | --- |
| | U/g | % | U/g | % |
| Hydrochloric acid | 2,000 | 100 | 920 | 46 |
| Sulfuric acid | 1,350 | 67.5 | 680 | 50.5 |
| Acetic acid | 1,950 | 97.5 | 983 | 50.4 |
| Phosphoric acid | 2,000 | 100 | 903 | 45.2 |
| Formic acid | 1,830 | 91.5 | 950 | 51.9 |
| (Water) | 945 | 47.3 | 295 | 31.2 |

What is claimed is:

1. An enzyme-active fibrous material which comprises a synthetic fiber of a partially aminoacetalized polyvinyl alcohol and an enzyme bonded thereto, the degree of aminoacetalization of the parially aminoacetalized polyvinyl alcohol being within the range from 0.5 to 10% by moles.

2. An enzyme-active fibrous material which comprises a synthetic fiber of a partially aminoacetalized polyvinyl alcohol and an enzyme bonded thereto, said synthetic fiber having a fineness in the range of from 0.05 to 1 μm in diameter.

3. An enzyme-active fibrous material which comprises a synthetic fiber of a partially aminoacetalized polyvinyl alcohol and an enzyme bonded thereto, said synthetic fiber being a composite filament composed of a partially aminoacetalized polyvinyl alcohol and a nonaminoacetalized polymer.

4. The enzyme-active fibrous material as set forth in claim 3 wherein the non-aminoacetalized polymer is a polyvinyl alcohol.

5. The enzyme-active fibrous material as set forth in claim 3 wherein the composite filament has a sheath-and-core structure.

6. The enzyme-active fibrous material as set forth in claim 3 wherein the composite filament has a side-by-side structure.

7. A material according to any one of claims 1-6 wherein said enzyme is selected from the group consisting of glucose isomerases, invertases, ureases, glucoamylases, glucose oxidases, lipases, ribonucleases, and proteases.

* * * * *